(12) United States Patent
Kim et al.

(10) Patent No.: US 12,122,886 B2
(45) Date of Patent: Oct. 22, 2024

(54) BIODEGRADABLE CAPSULE WITH SAFETY DUE TO NO IRRITATION TO HUMAN BODY AND MANUFACTURING METHOD THEREFOR

(71) Applicant: DAEHA MANTECH CO., LTD., Ansan-si (KR)

(72) Inventors: Hyun Kim, Ansan-si (KR); Gyeong-In Cho, Bucheon-si (KR); Seung Hwan Cha, Siheung-si (KR); Jung-Pyo Kim, Suwon-si (KR); Min-Ho Jong, Suwon-si (KR); Dong-Yeon Yang, Anyang-si (KR)

(73) Assignee: DAEHA MANTECH CO., LTD., Ansan-si (KR)

( * ) Notice: Subject to any disclaimer, the term of this patent is extended or adjusted under 35 U.S.C. 154(b) by 729 days.

(21) Appl. No.: 17/418,229

(22) PCT Filed: Jan. 16, 2020

(86) PCT No.: PCT/KR2020/000834
§ 371 (c)(1),
(2) Date: Jun. 24, 2021

(87) PCT Pub. No.: WO2020/149684
PCT Pub. Date: Jul. 23, 2020

(65) Prior Publication Data
US 2022/0112341 A1    Apr. 14, 2022

(30) Foreign Application Priority Data

Jan. 18, 2019 (KR) ........................ 10-2019-0006542
Nov. 15, 2019 (JP) ................................. 2019-207015

(51) Int. Cl.
   C08J 3/24      (2006.01)
   B01J 13/14     (2006.01)
   C11D 3/50      (2006.01)

(52) U.S. Cl.
CPC .............. *C08J 3/246* (2013.01); *B01J 13/14* (2013.01); *C11D 3/505* (2013.01); *C08J 2301/08* (2013.01); *C08J 2329/02* (2013.01); *C08J 2389/00* (2013.01)

(58) Field of Classification Search
CPC .... C08J 3/146; C08J 2301/08; C08J 2329/02; C08J 2389/00; C08J 2489/00; A61Q 13/00; C11D 3/505; A61K 8/87; A61K 8/791; A61K 8/85; A61K 8/64; A61K 8/11; A61K 2800/56; B01J 13/14
USPC ....................................................... 512/4, 1
See application file for complete search history.

(56) References Cited

U.S. PATENT DOCUMENTS

| | | |
|---|---|---|
| 11,077,417 B2 * | 8/2021 | Fuchs ................. A61K 9/5031 |
| 2007/0042182 A1 | 2/2007 | Markus et al. |
| 2013/0216596 A1 | 8/2013 | Viladot Petit et al. |
| 2015/0265541 A1 | 9/2015 | Park et al. |

FOREIGN PATENT DOCUMENTS

| | | | |
|---|---|---|---|
| KR | 10-2006-0031602 A | | 4/2006 |
| KR | 10-2011-0136490 A | | 12/2011 |
| KR | 10-2013-0138240 A | | 12/2013 |
| KR | 1020130138240 | * | 12/2013 |
| KR | 10-1366307 B1 | | 2/2014 |
| KR | 10-2015-0090038 A | | 8/2015 |
| KR | 10-2017-0071702 A | | 6/2017 |

OTHER PUBLICATIONS

Viladot et al, KR 1020130138240 Machine Translation, Dec. 18, 2013 (Year: 2013).*
International Search Report for PCT/KR2020/000834 mailed Sep. 7, 2020 from Korean Intellectual Property Office.

* cited by examiner

*Primary Examiner* — Jessica Whiteley
(74) *Attorney, Agent, or Firm* — Revolution IP, PLLC

(57) ABSTRACT

The present invention relates to: a biodegradable capsule which is a capsule having a form in which a capsule wall surrounds fragrance or oil, wherein a polymer, formed by the reaction of a fibrous polymer, a protein polymer, an aliphatic polyesterpolyol and an aliphatic crosslinking agent, constitutes the capsule wall of the capsule; and a manufacturing method thereof.

9 Claims, 1 Drawing Sheet

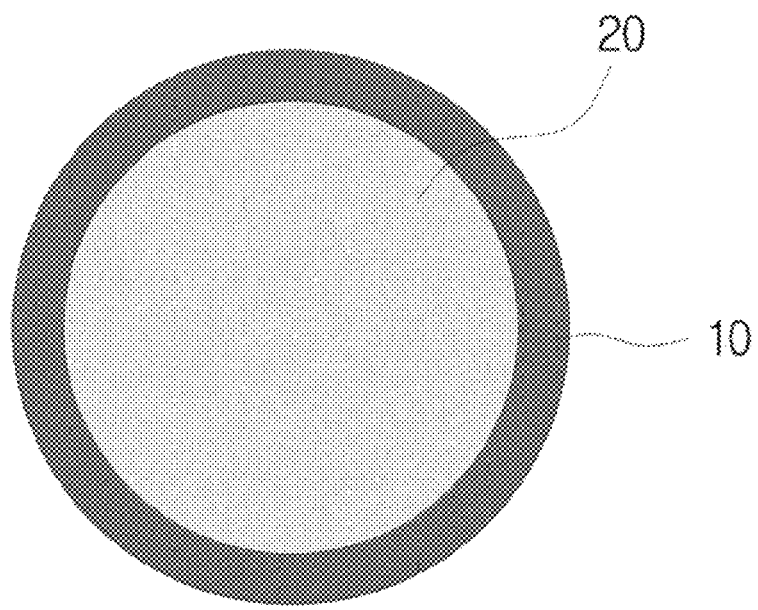

BIODEGRADABLE CAPSULE WITH SAFETY DUE TO NO IRRITATION TO HUMAN BODY AND MANUFACTURING METHOD THEREFOR

CROSS REFERENCE TO PRIOR APPLICATIONS

This application is the 35 U.S.C. 371 national stage of International application PCT/KR2020/000834 filed on Jan. 16, 2020; which claims priority to Korean Patent Application No. 10-2019-0006542 filed on Jan. 18, 2019, and Japanese Patent Application No. 2019-207015 filed on Nov. 15, 2019. The entire contents of each of the above-identified applications are hereby incorporated by reference.

TECHNICAL FIELD

The present invention relates to a biodegradable capsule and a preparation method thereof and, more particularly, to a biodegradable capsule and a preparation method thereof, in which a polymer, formed by the reaction of a fibrous polymer with excellent biodegradability, a protein polymer, an aliphatic polyesterpolyol, an aliphatic crosslinking agent, an aqueous natural surfactant solution, and amino acids, constitutes a capsule wall to form a capsule, and thus a capsule that has no irritation to the human body and is also biodegradable can be prepared.

BACKGROUND ART

Plastic materials are used in all areas of our lives, from daily necessities such as disposable packaging materials, toys, automobile interior materials, etc., to industrial materials. Although these plastic materials have made our lives convenient and comfortable in a short period of time, they are causing various environmental problems despite the short period of time. Among those environmental problems, the destruction and pollution of the marine ecosystem by plastics have emerged as a hot issue these days, since millions of tons of plastic waste flow into the ocean every year, and are broken down into small pieces without decomposition, combined with toxic substances, accumulated in the ocean, swallowed by plankton and small fish, travel through the ocean's food chain, and become serious enough to have harmful effects on humans. Accordingly, environmental organizations are putting an emphasis on the necessity of regulating the use of plastics, and countries are introducing laws, etc., to regulate the use of plastics. In addition, many companies are making efforts to reduce the use of plastic by replacing straws or cups with paper materials, or by replacing synthetic plastic scrubs used in cosmetics and toothpastes with natural scrubs such as coffee grounds, grain powder or the like.

Although most capsules are physically and chemically different from general plastic materials, those capsules go through a synthesis process and are transformed into substances that are difficult or slow to decompose, thereby increasing the possibility of causing environmental pollution.

Thus, it is required to improve the biodegradability of capsules, which are widely used as useful means for effectively protecting functional substances and facilitating the use thereof in the fields of household goods, cosmetics and the like, and to develop the capsules as materials that are safe for the human body.

To accomplish those purposes, many microencapsulation technologies have been developed so far, but poorly dependent on natural products only, thereby lowering the functionality as a capsule, or have been mainly based on the methods of using a crosslinking agent that is very harmful to the human body, such as glutaraldehyde, using a synthetic material with very low biodegradability, using a complicated process, using an organic solvent, and being poorly mass-produced, with a low or lack of biodegradability, safety, functionality and economy.

RELATED ART DOCUMENTS

Patent Documents

Korean Registered Patent Publication No. 10-1366307

DISCLOSURE

Technical Problem

An object of the present invention is to provide a biodegradable capsule and a preparation method thereof, which use a fibrous polymer, a protein polymer, amino acids and an aqueous natural surfactant solution, which are easily decomposed by microorganisms or enzymes and are bio-compatible substances, and also use a small amount of biodegradable aliphatic polyesterpolyol and aliphatic crosslinking agent to more efficiently implement the functionality of the capsule, such that the resulting capsule is excellently biodegradable, safe for the human body, and enables the effective use of functionality.

Technical Solution

The present invention may provide a biodegradable capsule which is a capsule having a form in which a capsule wall surrounds fragrance or oil, wherein a polymer, formed by reaction of a fibrous polymer, a protein polymer, an aliphatic polyesterpolyol, an aliphatic crosslinking agent, an aqueous natural surfactant solution, and amino acids, constitutes a capsule wall of the capsule, and the capsule has a diameter of 0.1-300 μm.

The fibrous polymer may include at least one material selected from the group consisting of methyl cellulose, ethyl ether cellulose, ethyl-2-hydroxyethyl cellulose, hydroxymethyl cellulose, hydroxyethyl cellulose, hydroxyethyl methylcellulose, hydroxypropyl cellulose, hydroxypropyl methyl cellulose, hydroxybutyl methylcellulose, 2-aminoethyl 2-hydroxypropyl cellulose, hemicellulose, 6-carboxy cellulose, carboxymethyl cellulose, carboxymethyl ether cellulose, cellulose acetate, alginate and sorbitol.

The protein polymer may include at least one material selected from the group consisting of hydrolyzed oat protein, hydrolyzed corn protein, hydrolyzed yeast protein, hydrolyzed soy protein, hydrolyzed wheat protein, hydrolyzed rice protein, hydrolyzed potato protein, hydrolyzed silk protein, hydrolyzed collagen, hydrolyzed keratin, hydrolyzed elastin, hydrolyzed casein, laurdimonium hydroxypropyl hydrolyzed wheat protein, laurdimonium hydroxypropyl hydrolyzed soy protein, lauryl dimonium hydroxypropyl hydrolyzed collagen, myristoyl hydrolyzed collagen, olivoyl hydrolyzed wheat protein, cocodimonium hydroxypropyl hydrolyzed wheat protein, TEA-cocoyl hydrolyzed collagen, potassium undecylenoyl hydrolyzed collagen, potassium cocoyl hydrolyzed collagen, potassium palmitoyl hydrolyzed wheat protein, hydroxypropyl trimonium hydrolyzed silk and hydroxypropyl trimonium hydrolyzed collagen.

The aliphatic polyesterpolyol may include aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, maleic anhydride, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol.

The aliphatic crosslinking agent may include at least one material selected from the group consisting of 4,4'-dicyclohexylmethane diisocyanate, trans-1,4-cyclohexanediisocyanate, isophorone diisocyanate, hexamethylene diisocyanate, trimethylhexamethylene diisocyanate and 1,3-bis(isocyanatomethyl)-cyclohexane.

The aqueous natural surfactant solution may include at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside, decyl glucoside, sodium cocoyl glutamate and potassium cocoyl glycinate.

The amino acids may include at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

In addition, the present invention may provide a method for preparing a biodegradable capsule, the method comprising: (a) mixing fragrance or oil, a fibrous polymer, a protein polymer and an aliphatic polyesterpolyol; (b) mixing an aliphatic crosslinking agent in a mixture of the fragrance or oil, the fibrous polymer, the protein polymer and the aliphatic polyesterpolyol; (c) mixing and emulsifying an aqueous natural surfactant solution in the mixture of the aliphatic cross-linking agent to form an oil/water emulsion; and (d) adding amino acids to the oil/water emulsion and reacting to obtain a capsule.

It is preferable that the fibrous polymer is mixed in an amount of 1-20 parts by weight based on 100 parts by weight of fragrance or oil.

The fibrous polymer may include at least one material selected from the group consisting of methyl cellulose, ethyl ether cellulose, ethyl-2-hydroxyethyl cellulose, hydroxymethyl cellulose, hydroxyethyl cellulose, hydroxyethyl methylcellulose, hydroxypropyl cellulose, hydroxypropyl methyl cellulose, hydroxybutyl methylcellulose, 2-aminoethyl 2-hydroxypropyl cellulose, hemicellulose, 6-carboxy cellulose, carboxymethyl cellulose, carboxymethyl ether cellulose, cellulose acetate and alginate.

It is preferable that the protein polymer is mixed in an amount of 1-20 parts by weight based on 100 parts by weight of fragrance or oil.

The protein polymer may include at least one material selected from the group consisting of hydrolyzed oat protein, hydrolyzed corn protein, hydrolyzed yeast protein, hydrolyzed soy protein, hydrolyzed wheat protein, hydrolyzed rice protein, hydrolyzed potato protein, hydrolyzed silk protein, hydrolyzed collagen, hydrolyzed keratin, hydrolyzed elastin, hydrolyzed casein, laurdimonium hydroxypropyl hydrolyzed wheat protein, laurdimonium hydroxypropyl hydrolyzed soy protein, lauryl dimonium hydroxypropyl hydrolyzed collagen, myristoyl hydrolyzed collagen, olivoyl hydrolyzed wheat protein, cocodimonium hydroxypropyl hydrolyzed wheat protein, TEA-cocoyl hydrolyzed collagen, potassium undecylenoyl hydrolyzed collagen, potassium cocoyl hydrolyzed collagen, potassium palmitoyl hydrolyzed wheat protein, hydroxypropyl trimonium hydrolyzed silk and hydroxypropyl trimonium hydrolyzed collagen.

It is preferable that the aliphatic polyesterpolyol is mixed in an amount of 1-5 parts by weight based on 100 parts by weight of fragrance or oil.

The aliphatic polyesterpolyol may include aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, maleic anhydride, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol.

It is preferable that the aliphatic crosslinking agent is mixed in an amount of 0.1-5 parts by weight based on 100 parts by weight of fragrance or oil, and the aliphatic crosslinking agent may include at least one material selected from the group consisting of 4,4'-dicyclohexylmethane diisocyanate, trans-1,4-cyclohexanediisocyanate, isophorone diisocyanate, hexamethylene diisocyanate, trimethylhexamethylene diisocyanate and 1,3-bis(isocyanatomethyl)-cyclohexane.

The aqueous natural surfactant solution may be an aqueous solution obtained by mixing 1-10 parts by weight of a natural surfactant based on 100 parts by weight of fragrance or oil and adding 10-90 parts by weight of water based on 100 parts by weight of fragrance or oil.

The natural surfactant may include at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside, decyl glucoside, sodium cocoyl glutamate and potassium cocoyl glycinate.

It is preferable that the amino acids are mixed in an amount of 0.1-5 parts by weight based on 100 parts by weight of fragrance or oil.

The amino acids may include at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

The pH of the oil/water emulsion may be adjusted with an acid or a base in above step (c) or above step (d).

It is preferable that the reaction is performed at a temperature of 30 to 50° C. in above step (d).

Advantageous Effects

According to the present invention, since a polymer, formed by the reaction of a fibrous polymer with excellent biodegradability, a protein polymer, an aliphatic polyesterpolyol, an aliphatic crosslinking agent, an aqueous natural surfactant solution, and amino acids, constitutes a capsule wall to form a capsule, a capsule that has no irritation to the human body and is also biodegradable can be manufactured. By using a fibrous polymer, a protein polymer, an aqueous natural surfactant solution and amino acids, which are easily decomposed by microorganisms or enzymes and are human-friendly, and also using a small amount of biodegradable aliphatic polyesterpolyol and aliphatic crosslinking agent to more efficiently implement the functionality of the capsule, the capsule which is excellently biodegradable, safe for the human body, and enables the effective use of functionality, can be prepared.

In addition, according to the present invention, by using a small amount of biodegradable aliphatic polyesterpolyol and aliphatic crosslinking agent and reacting at a relatively low temperature of 30-50° C., capsule functionality can be more effectively implemented, side effects occurring during a production process can be prevented, and production efficiency can be improved.

DESCRIPTION OF DRAWINGS

FIG. 1 is a view showing a biodegradable capsule according to a preferred embodiment of the present invention.

BEST MODE

A biodegradable capsule according to a preferred embodiment of the present invention may be a capsule having a form in which a capsule wall surrounds fragrance or oil, and a polymer, formed by reaction of a fibrous polymer, a protein polymer, an aliphatic polyesterpolyol, an aliphatic crosslinking agent, an aqueous natural surfactant solution, and amino acids, may constitute a capsule wall of the capsule, and the capsule may have a diameter of 0.1-300 μm.

A method for preparing a biodegradable capsule according to a preferred embodiment of the present invention may include: (a) mixing fragrance or oil, a fibrous polymer, a protein polymer and an aliphatic polyesterpolyol; (b) mixing an aliphatic crosslinking agent in a mixture of the fragrance or oil, the fibrous polymer, the protein polymer and the aliphatic polyesterpolyol; (c) mixing and emulsifying an aqueous natural surfactant solution in the mixture of the aliphatic cross-linking agent to form an oil/water emulsion; and (d) adding amino acids to the oil/water emulsion and reacting to obtain a capsule.

MODE FOR INVENTION

Hereinafter, preferred embodiments according to the present invention will be described in detail. However, the following embodiments are provided so that those of ordinary skill in the art can fully understand the present invention, and may be modified in various other forms, and the scope of the present invention is not limited to the embodiments described below.

When it is said that any one component "includes" another component in the detailed description or claims of the invention, it is not construed as being limited to only the component unless otherwise stated, but it should be understood that other components are further included.

A biodegradable capsule according to a preferred embodiment of the present invention may be a capsule having a form in which a capsule wall surrounds fragrance or oil, and a polymer, formed by reaction of a fibrous polymer, a protein polymer, an aliphatic polyesterpolyol, an aliphatic crosslinking agent, an aqueous natural surfactant solution, and amino acids, may constitute a capsule wall of the capsule, and the capsule may have a diameter of 0.1-300 μm.

The fibrous polymer may include at least one material selected from the group consisting of methyl cellulose, ethyl ether cellulose, ethyl-2-hydroxyethyl cellulose, hydroxymethyl cellulose, hydroxyethyl cellulose, hydroxyethyl methylcellulose, hydroxypropyl cellulose, hydroxypropyl methyl cellulose, hydroxybutyl methylcellulose, 2-aminoethyl 2-hydroxypropyl cellulose, hemicellulose, 6-carboxy cellulose, carboxymethyl cellulose, carboxymethyl ether cellulose, cellulose acetate and alginate.

The protein polymer may include at least one material selected from the group consisting of hydrolyzed oat protein, hydrolyzed corn protein, hydrolyzed yeast protein, hydrolyzed soy protein, hydrolyzed wheat protein, hydrolyzed rice protein, hydrolyzed potato protein, hydrolyzed silk protein, hydrolyzed collagen, hydrolyzed keratin, hydrolyzed elastin, hydrolyzed casein, laurdimonium hydroxypropyl hydrolyzed wheat protein, laurdimonium hydroxypropyl hydrolyzed soy protein, lauryl dimonium hydroxypropyl hydrolyzed collagen, myristoyl hydrolyzed collagen, olivoyl hydrolyzed wheat protein, cocodimonium hydroxypropyl hydrolyzed wheat protein, TEA-cocoyl hydrolyzed collagen, potassium undecylenoyl hydrolyzed collagen, potassium cocoyl hydrolyzed collagen, potassium palmitoyl hydrolyzed wheat protein, hydroxypropyl trimonium hydrolyzed silk and hydroxypropyl trimonium hydrolyzed collagen.

The aliphatic polyesterpolyol may include aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, maleic anhydride, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol.

The aliphatic crosslinking agent may include at least one material selected from the group consisting of 4,4'-dicyclohexylmethane diisocyanate, trans-1,4-cyclohexanediisocyanate, isophorone diisocyanate, hexamethylene diisocyanate, trimethylhexamethylene diisocyanate and 1,3-bis(isocyanatomethyl)-cyclohexane.

The aqueous natural surfactant solution may include at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside, decyl glucoside, sodium cocoyl glutamate and potassium cocoyl glycinate.

The amino acids may include at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

A method for preparing a biodegradable capsule according to a preferred embodiment of the present invention may include: (a) mixing fragrance or oil, a fibrous polymer, a protein polymer and an aliphatic polyesterpolyol; (b) mixing an aliphatic crosslinking agent in a mixture of the fragrance or oil, the fibrous polymer, the protein polymer and the aliphatic polyesterpolyol; (c) mixing and emulsifying an aqueous natural surfactant solution in the mixture of the aliphatic cross-linking agent to form an oil/water emulsion; and (d) adding amino acids to the oil/water emulsion and reacting to obtain a capsule.

It is preferable that the fibrous polymer is mixed in an amount of 1-20 parts by weight based on 100 parts by weight of fragrance or oil.

The fibrous polymer may include at least one material selected from the group consisting of methyl cellulose, ethyl ether cellulose, ethyl-2-hydroxyethyl cellulose, hydroxymethyl cellulose, hydroxyethyl cellulose, hydroxyethyl methylcellulose, hydroxypropyl cellulose, hydroxypropyl methyl cellulose, hydroxybutyl methylcellulose, 2-aminoethyl 2-hydroxypropyl cellulose, hemicellulose, 6-carboxy cellulose, carboxymethyl cellulose, carboxymethyl ether cellulose, cellulose acetate and alginate.

It is preferable that the protein polymer is mixed in an amount of 1-20 parts by weight based on 100 parts by weight of fragrance or oil.

The protein polymer may include at least one material selected from the group consisting of hydrolyzed oat protein, hydrolyzed corn protein, hydrolyzed yeast protein, hydrolyzed soy protein, hydrolyzed wheat protein, hydrolyzed rice protein, hydrolyzed potato protein, hydrolyzed silk protein, hydrolyzed collagen, hydrolyzed keratin, hydrolyzed elastin, hydrolyzed casein, laurdimonium hydroxypropyl hydrolyzed wheat protein, laurdimonium hydroxypropyl hydrolyzed soy protein, lauryl dimonium hydroxypropyl hydrolyzed collagen, myristoyl hydrolyzed collagen, olivoyl hydrolyzed wheat protein, cocodimonium hydroxypropyl hydrolyzed wheat protein, TEA-cocoyl hydrolyzed collagen, potassium undecylenoyl hydrolyzed collagen, potassium cocoyl hydrolyzed collagen, potassium palmitoyl hydrolyzed wheat protein, hydroxypropyl trimonium hydrolyzed silk and hydroxypropyl trimonium hydrolyzed collagen.

It is preferable that the aliphatic polyesterpolyol is mixed in an amount of 1-5 parts by weight based on 100 parts by weight of fragrance or oil.

The aliphatic polyesterpolyol may include aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, maleic anhydride, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol.

It is preferable that the aliphatic crosslinking agent is mixed in an amount of 0.1-5 parts by weight based on 100 parts by weight of fragrance or oil, and the aliphatic crosslinking agent may include at least one material selected from the group consisting of 4,4'-dicyclohexylmethane diisocyanate, trans-1,4-cyclohexanediisocyanate, isophorone diisocyanate, hexamethylene diisocyanate, trimethylhexamethylene diisocyanate and 1,3-bis(isocyanatomethyl)-cyclohexane.

The aqueous natural surfactant solution may be an aqueous solution obtained by mixing 1-10 parts by weight of a natural surfactant based on 100 parts by weight of fragrance or oil and adding 10-90 parts by weight of water based on 100 parts by weight of fragrance or oil.

The natural surfactant may include at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside, decyl glucoside, sodium cocoyl glutamate and potassium cocoyl glycinate.

It is preferable that the amino acids are mixed in an amount of 0.1-5 parts by weight based on 100 parts by weight of fragrance or oil.

The amino acids may include at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

The pH of the oil/water emulsion may be adjusted with an acid or a base in above step (c) or above step (d).

It is preferable that the reaction is performed at a temperature of 30 to 50° C. in above step (d).

Hereinafter, the method for preparing a biodegradable capsule according to a preferred embodiment of the present invention will be described in more detail.

The present invention provides the biodegradable capsule, which has excellent biodegradability, is safe for the human body, and enables the effective use of functionality, and the preparation method thereof.

FIG. 1 is a view showing a biodegradable capsule according to a preferred embodiment of the present invention.

Referring to FIG. 1, the biodegradable capsule according to a preferred embodiment of the present invention may be a capsule having a form in which a capsule wall 10 surrounds fragrance or oil 20, and a polymer, formed by reaction of a fibrous polymer, a protein polymer, an aliphatic polyesterpolyol, an aliphatic crosslinking agent, an aqueous natural surfactant solution, and amino acids, may constitute the capsule wall 10 of the capsule, and the capsule may have a diameter of 0.1-300 μm.

The fibrous polymer may include at least one material selected from the group consisting of methyl cellulose, ethyl ether cellulose, ethyl-2-hydroxyethyl cellulose, hydroxymethyl cellulose, hydroxyethyl cellulose, hydroxyethyl methylcellulose, hydroxypropyl cellulose, hydroxypropyl methyl cellulose, hydroxybutyl methylcellulose, 2-aminoethyl 2-hydroxypropyl cellulose, hemicellulose, 6-carboxy cellulose, carboxymethyl cellulose, carboxymethyl ether cellulose, cellulose acetate and alginate.

The protein polymer may include at least one material selected from the group consisting of hydrolyzed oat protein, hydrolyzed corn protein, hydrolyzed yeast protein, hydrolyzed soy protein, hydrolyzed wheat protein, hydrolyzed rice protein, hydrolyzed potato protein, hydrolyzed silk protein, hydrolyzed collagen, hydrolyzed keratin, hydrolyzed elastin, hydrolyzed casein, laurdimonium hydroxypropyl hydrolyzed wheat protein, laurdimonium hydroxypropyl hydrolyzed soy protein, lauryl dimonium hydroxypropyl hydrolyzed collagen, myristoyl hydrolyzed collagen, olivoyl hydrolyzed wheat protein, cocodimonium hydroxypropyl hydrolyzed wheat protein, TEA-cocoyl hydrolyzed collagen, potassium undecylenoyl hydrolyzed collagen, potassium cocoyl hydrolyzed collagen, potassium palmitoyl hydrolyzed wheat protein, hydroxypropyl trimonium hydrolyzed silk and hydroxypropyl trimonium hydrolyzed collagen.

The aliphatic polyesterpolyol may include aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, maleic anhydride, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol.

The aliphatic crosslinking agent may include at least one material selected from the group consisting of 4,4'-dicyclohexylmethane diisocyanate, trans-1,4-cyclohexanediisocyanate, isophorone diisocyanate, hexamethylene diisocyanate, trimethylhexamethylene diisocyanate and 1,3-bis(isocyanatomethyl)-cyclohexane.

The aqueous natural surfactant solution may include at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside (compound obtained by condensation reaction of palm kernel acid and coconut acid with glucose), decyl glucoside, sodium cocoyl glutamate and potassium cocoyl glycinate.

The amino acids may include at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

To prepare the biodegradable capsule according to a preferred embodiment of the present invention, the fragrance or oil, the fibrous polymer, the protein polymer and the aliphatic polyesterpolyol may be mixed together.

The fragrance may be a material such as an aromatic herb fragrance, a rose fragrance, a jasmine fragrance, a lavender fragrance, a mint fragrance, a banana fragrance, an apple fragrance, a strawberry fragrance, a vanilla fragrance, a mixture thereof, etc.

The oil may be at least one material selected from the group consisting of natural oil, synthetic oil, and oily oil. The natural oil may be jojoba oil, olive oil, rosehip oil, camellia oil, argan oil, avocado oil, coconut oil, almond oil, tea tree oil, eucalyptus oil, rosemary oil, lavender oil, a mixture thereof, etc. The synthetic oil may be ester oil, silicone oil, a mixture thereof, etc. The oily oil may be a material used as a cosmetic raw material, such as retinol, ceramide, ethylhexyl salicylate, ethylhexyl methoxycinnamate, alpha-bisabolol, oil-soluble licorice extract, a mixtures thereof, etc.

It is preferable that the fibrous polymer is mixed in an amount of 1-20 parts by weight based on 100 parts by weight of fragrance or oil. The fibrous polymer may be a linear chain polysaccharide polymer compound in which hundreds to thousands of glucose units are linked by a glycosidic bond, and may have excellent reactivity with other compounds, thereby making a great contribution to stabilizing the material to be loaded in a capsule due to the polymer formed after a reaction. In addition, after the capsule is applied and used in a product, there is an advantage that the capsule can be easily biodegradable by microorganisms or enzymes present in nature. Accordingly, it is easy to control the reactivity and biodegradability of the capsule by containing a fibrous polymer.

The fibrous polymer may include at least one material selected from the group consisting of methyl cellulose, ethyl ether cellulose, ethyl-2-hydroxyethyl cellulose, hydroxymethyl cellulose, hydroxyethyl cellulose, hydroxyethyl methylcellulose, hydroxypropyl cellulose, hydroxypropyl methyl cellulose, hydroxybutyl methylcellulose, 2-aminoethyl 2-hydroxypropyl cellulose, hemicellulose, 6-carboxy cellulose, carboxymethyl cellulose, carboxymethyl ether cellulose, cellulose acetate and alginate.

It is preferable that the protein polymer is mixed in an amount of 1-20 parts by weight based on 100 parts by weight of fragrance or oil. The protein polymer may have a form in which high molecular weight proteins are hydrolyzed and thus soluble in water, and have low crystallinity and high flexibility due to irregular repeating units compared to synthetic polymers, and thus may be preferably selected from those protein polymers advantageous for biodegradation.

The protein polymer may include at least one material selected from the group consisting of hydrolyzed oat protein, hydrolyzed corn protein, hydrolyzed yeast protein, hydrolyzed soy protein, hydrolyzed wheat protein, hydrolyzed rice protein, hydrolyzed potato protein, hydrolyzed silk protein, hydrolyzed collagen, hydrolyzed keratin, hydrolyzed elastin, hydrolyzed casein, laurdimonium hydroxypropyl hydrolyzed wheat protein, laurdimonium hydroxypropyl hydrolyzed soy protein, lauryl dimonium hydroxypropyl hydrolyzed collagen, myristoyl hydrolyzed collagen, olivoyl hydrolyzed wheat protein, cocodimonium hydroxypropyl hydrolyzed wheat protein, TEA-cocoyl hydrolyzed collagen, potassium undecylenoyl hydrolyzed collagen, potassium cocoyl hydrolyzed collagen, potassium palmitoyl hydrolyzed wheat protein, hydroxypropyl trimonium hydrolyzed silk and hydroxypropyl trimonium hydrolyzed collagen.

It is preferable that the aliphatic polyesterpolyol is mixed in an amount of 1-5 parts by weight based on 100 parts by weight of fragrance or oil. The aliphatic polyesterpolyol may have both hydrophobicity and hydrophilicity, have an active site in a molecular chain, and have structural flexibility, so as to provide an excellently biodegradable polymer, thereby complementing a disadvantage of the protein polymer having weak physical strength and low uniformity. When the capsule is applied to the product, the capsule may not be destroyed, but when the product to which the capsule is applied is used, the capsule may be easily destroyed by a physical force, and thus the oil-soluble material therein may be effectively released.

It is preferable that the aliphatic polyesterpolyol is aliphatic unsaturated polyesterpolyol which is obtained by esterification dehydration condensation reaction between a bivalent or more acid and a bivalent or more alcohol. For example, the aliphatic polyesterpolyol may be aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, maleic anhydride, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol.

An aliphatic crosslinking agent may be mixed in a mixture of the fragrance or oil, the fibrous polymer, the protein polymer and the aliphatic polyesterpolyol.

It is preferable that the aliphatic crosslinking agent is mixed in an amount of 0.1-5 parts by weight based on 100 parts by weight of fragrance or oil. The aliphatic crosslinking agent may be structurally flexible and partially form a polyurethane-based material based on polyester, which is more excellently biodegradable than polyether, so as to increase the strength of the capsule even by using a remarkably smaller amount than when forming a general plastic material, thereby controlling the release of an oil-soluble material with functionality and reducing a reaction time to secure functionality and economic efficiency.

The aliphatic crosslinking agent may include at least one material selected from the group consisting of 4,4'-dicyclohexylmethane diisocyanate, trans-1,4-cyclohexanediisocyanate, isophorone diisocyanate, hexamethylene diisocyanate, trimethylhexamethylene diisocyanate and 1,3-bis(isocyanatomethyl)-cyclohexane.

An aqueous natural surfactant solution may be mixed in a mixture, in which the aliphatic crosslinking agent is mixed and emulsified to form an oil/water emulsion (Oil/Water, O/W or Oil in Water). At this time, the pH may be adjusted with an acid or a base. It is preferable that the pH is adjusted to pH 3 to 5 when acidic conditions are required, and to pH 9 to 11 when basic conditions are required depending on the isoelectric point or properties of the material. Proteins and amino acid-based materials may have an isoelectric point where the charge of ionic amino acids present in the material varies depending on the pH, and thus ionicity changes and solubility and reactivity vary to affect the reaction conditions of the capsule and compatibility with other substances. Thus, it is necessary to adjust the pH according to the material to be mixed.

By the emulsification, an oil/water (Oil/Water, O/W or Oil in Water) emulsion may be formed. The mixing may be performed using a homomixer or the like, and may be preferably performed at a speed of about 1000 to 5000 rpm.

It is preferable that the aqueous natural surfactant solution is an aqueous solution obtained by mixing 1-10 parts by weight of a natural surfactant based on 100 parts by weight of fragrance or oil and adding 10-90 parts by weight of water based on 100 parts by weight of fragrance or oil. Compared to synthetic surfactants, natural surfactants may have an advantageous structure for biodegradation and be biocompatible, and thus natural surfactants may be safe and have additional functions such as moisturizing, conditioning or the like.

The natural surfactant may include at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside (compound obtained by condensation reaction of palm kernel acid and coconut acid with glucose), decyl glucoside, sodium cocoyl glutamate and potassium cocoyl glycinate.

Amino acids may be added to the oil/water emulsion and reacted to obtain a capsule. At this time, the pH may be adjusted with an acid or a base. It is preferable that the pH is adjusted to pH 3 to 5 when acidic conditions are required, and to pH 9 to 11 when basic conditions are required depending on the isoelectric point or properties of the material. It is preferable that the reaction is performed at a temperature of 30 to 50° C. Proteins and amino acid-based materials may have an isoelectric point where the charge of ionic amino acids present in the material varies depending on the pH, and thus ionicity changes and solubility and reactivity vary to affect the reaction conditions of the capsule and compatibility with other substances. Thus, it is necessary to adjust the pH according to the material to be mixed. It is preferable that the reaction is performed while stirring at a speed of about 300 to 500 rpm. As the reaction time elapses, a capsule wall may be formed through hardening and finally a biodegradable capsule may be formed.

It is preferable that the amino acids are mixed in an amount of 0.1-5 parts by weight based on 100 parts by weight of fragrance or oil. Amino acids are low-molecular substances, which do not require a hydrolysis process, and are less disturbed by side chains, and thus the amino acids are easy to show activity by microorganisms, are more easily decomposed by microorganisms, and lower the fluidity limitation and crystallinity of the polymer chain due to the crosslinking of the polymer, thereby increasing the accessibility of microorganisms. In addition, due to the presence of amino groups, it is possible to form a hard capsule wall with good reactivity, which makes it easy to control the release of fragrance or oil, and enables a low-temperature reaction and shortening of reaction time.

The amino acids may include at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

It is preferable that the reaction is performed at a temperature of 30 to 50° C. The reaction at a low temperature may prevent side reactions and deformation of polymer materials that may occur in high-temperature reactions, and it is possible to efficiently encapsulate highly oxidized or volatile materials.

Capsules prepared above may be excellently biodegradable, safe for the human body, more effectively implement the functionality of the capsules, prevent side effects occurring in a production process, and improve production efficiency.

According to the present invention, a polymer, formed by reaction of a fibrous polymer, a protein polymer, an aliphatic polyesterpolyol, an aliphatic crosslinking agent, an aqueous natural surfactant solution, and amino acids, may constitute a capsule wall of the capsule, and thus it may be possible to prepare a biodegradable capsule, which is excellently biodegradable, safe, and easy to protect and use a functional substance (fragrance or oil).

In the biodegradable capsule prepared according to the present invention, a polymer, formed by reaction of a fibrous polymer, a protein polymer, an aliphatic polyesterpolyol, an aliphatic crosslinking agent, an aqueous natural surfactant solution, and amino acids, may constitute a capsule wall of the capsule to protect fragrance or oil.

Hereinafter, embodiments according to the present invention are specifically presented, and the present invention is not limited to the following examples.

Example 1

In a 500 ml beaker, 100 g of aroma herb fragrance, 10 g of methyl cellulose, 10 g of hydrolyzed wheat protein, and 2 g of aliphatic polyesterpolyol obtained by esterification dehydration condensation reaction of adipic acid and 1,3-butylene glycol were uniformly mixed, and then 1 g of ready-made isophorone diisocyanate was further mixed, after which an aqueous natural surfactant solution made by mixing 5 g of babasuamidopropyl betaine, a natural surfactant, and 45 g of water was added and stirred for about 20 minutes at a speed of 3,000 rpm using a homomixer, so as to prepare an oil/water emulsion.

The oil/water emulsion was added into a 1 l four-necked flask, and a small amount of caustic soda was added to adjust the pH to 9-11, after which 0.5 g of aspartic acid was added to adjust a reaction temperature to 40° C. and reacted while stirring for about 3 hours, so as to prepare a biodegradable capsule.

Example 2

In a 500 ml beaker, 100 g of aroma herb fragrance, 10 g of methyl cellulose, 10 g of hydrolyzed oat protein, and 2 g of aliphatic polyesterpolyol obtained by esterification dehydration condensation reaction of adipic acid and pentanediol were uniformly mixed, and then 1 g of ready-made isophorone diisocyanate was further mixed, after which an aqueous natural surfactant solution made by mixing 5 g of babasuamidopropyl betaine, a natural surfactant, and 45 g of water was added and stirred for about 20 minutes at a speed of 3,000 rpm using a homomixer, so as to prepare an oil/water emulsion.

The oil/water emulsion was added into a 1 l four-necked flask, and a small amount of acetic acid was added to adjust the pH to 3-5, after which 1.5 g of arginine was added to adjust a reaction temperature to 40° C. and reacted while stirring for about 3 hours, so as to prepare a biodegradable capsule.

Example 3

In a 500 ml beaker, 100 g of aroma herb fragrance, 10 g of methyl cellulose, 10 g of laurdimonium hydroxypropyl hydrolyzed wheat protein, and 2 g of aliphatic polyesterpolyol obtained by esterification dehydration condensation reaction of adipic acid and sorbitol were uniformly mixed, and then 1 g of ready-made isophorone diisocyanate was further mixed, after which an aqueous natural surfactant solution made by mixing 5 g of babasuamidopropyl betaine, a natural surfactant, and 45 g of water was added and stirred for about 20 minutes at a speed of 3,000 rpm using a homomixer, so as to prepare an oil/water emulsion.

The oil/water emulsion was added into a 1 l four-necked flask, and a small amount of acetic acid was added to adjust the pH to 3-5, after which 1.5 g of glutamine was added to adjust a reaction temperature to 40° C. and reacted while stirring for about 3 hours, so as to prepare a biodegradable capsule.

Comparative Example 1

In a 1 l 4-necked flask, 10 g of melamine, 40 g of distilled water, 20 g of 35 wt % aqueous formaldehyde solution and a small amount of sodium hydroxide were added to adjust the pH to 8-10, and stirred at 80° C. for 30 minutes so as to obtain a melamine-formaldehyde prepolymer.

In a separate 1 l beaker, 200 g of an emulsifier, which contains 5 wt % of ethylene-maleic acid copolymer resin (trade name: EMA-31, manufactured by Monsanto) and serves as an anionic surfactant, was prepared, after which 100 g of aroma herb fragrance was added thereto and stirred at a speed of 3,000 rpm for about 20 minutes by using a homomixer to prepare an oil/water emulsion.

The melamine-formaldehyde prepolymer and the oil/water emulsion were mixed together and then stirred at 70° C. for about 3 hours to harden a capsule wall, thereby preparing melamine capsules.

Comparative Example 2

The 50 g of food starch substituted with n-octenyl (substitution rate 0.005) was dissolved in 50 g of water. In order to increase the density of starch in the resulting solution, 5 g of NaCl was added to prepare an aqueous starch solution which is well-dissolved as a single phase.

The 100 g of aroma herb fragrance was added to the aqueous starch solution and stirred at a high speed of 3000 rpm for 20 minutes with a homomixer to carry out emulsification.

The 5 g of glutardialdehyde, which serves as a cross-linking agent, was added to a solution, in which the aroma herb fragrance was emulsified in the aqueous starch solution, and cross-linked at 3000 rpm for 40 minutes to prepare capsules.

<Comparative Experiment>

Each of the capsules prepared according to Examples 1 to 3 and Comparative Examples 1 and 2 was evaluated for biodegradability, skin irritation and scent diffusion performance.

[Method and Criteria for Biodegradability Measurement]

Each capsule prepared in above Examples 1 to 3 and Comparative Examples 1 and 2 was evaluated by KS I ISO 9408, which measures the final aerobic biodegradation of organic compounds in a liquid medium by measuring an oxygen demand of a water-tight respiration meter, and OECD 301F method equivalent thereto.

Specifically, the evaluation was performed as shown in Table 1 according to the measured values of biodegradability.

○: The biodegradability value is 60% or more compared to the reference material.

Δ: The biodegradability value is 30% or more and less than 60% compared to the reference material.

X: The biodegradability value is less than 30% compared to the reference material.

[Skin Irritation Test Method and Evaluation Criteria]

Each capsule prepared in above Examples 1 to 3 and Comparative Examples 1 and 2 was applied to the backs of 31 subjects for 24 hours, and observed 30 minutes, 24 hours, and 48 hours after the patch was removed, and then evaluated as non/slight/mild/moderate/strong according to the criteria applied from the International Contact Dermatitis Research Group (ICDRG) and the Personal Care Products Council (PCPC), and the results thereof are shown in Table 1.

[Scent Diffusion Performance Test Method and Evaluation Criteria]

Each capsule prepared in above Examples 1 to 3 and Comparative Examples 1 and 2 was added 0.5% to a fragrance-free highly concentrated fabric softener base, after which towel was washed according to a standard dose of highly concentrated fabric softener and dried at room temperature for 24 hours, so as to prepare a sample for a scent diffusion performance evaluation.

The scent diffusion performance was evaluated for each capsule prepared in Examples 1 to 3 and Comparative Examples 1 and 2 among a panel of 30 subjects, who were asked to rub each of the prepared towels 5 times with hands, smell with a nose, and give scores on a scale of 1 to 5 points (5: very strong, 4: strong, 3: moderate, 2: slightly weak, 1: weak, 0: none) for the sensory level of smell felt by the nose, after which a final evaluation was made by the sum of scores (150-101 points: good, 100-51 points: average, 50-0: bad).

TABLE 1

| Evaluation Item | Example 1 | Example 2 | Example 3 | Comparative Example 1 | Comparative Example 2 |
|---|---|---|---|---|---|
| Biodegradability | ○ | ○ | ○ | X | Δ |
| Skin irritation | Non | Non | Non | Slight | Moderate |
| Scent diffusing performance | Good | Good | Good | Average | Bad |

As shown in above Table 1, in the case of Examples 1 to 3, the capsules were excellent in biodegradability without skin irritation compared to Comparative Examples 1 and 2 and thus were evaluated as excellently biodegradable and safe for the human body.

In addition, it was found that the capsules of Examples 1 to 3 show a better scent diffusion performance than those of Comparative Examples 1 and 2, and thus fragrance or oil can be used most effectively.

As described above, although preferred embodiments of the present invention have been described in detail, the present invention is not limited to the above embodiments, and various modifications are possible by those skilled in the art.

INDUSTRIAL APPLICABILITY

According to the present invention, since a polymer, formed by the reaction of a fibrous polymer with excellent biodegradability, a protein polymer, an aliphatic polyesterpolyol, an aliphatic crosslinking agent, an aqueous natural surfactant solution, and amino acids, constitutes a capsule wall to form a capsule, a capsule that has no irritation to the human body and is also biodegradable can be manufactured with industrial applicability.

What is claimed is:

1. A biodegradable capsule, which is a capsule having a form in which a capsule wall surrounds fragrance or oil, wherein a polymer, formed by reaction of
   a fibrous polymer mixed in an amount of 1-20 parts by weight based on 100 parts by weight of the fragrance or oil, and comprising at least one material selected from the group consisting of ethyl ether cellulose, hydroxyethyl methylcellulose, hydroxybutyl methylcellulose, 2-aminoethyl 2-hydroxypropyl cellulose, hemicellulose, 6-carboxy cellulose, carboxymethyl ether cellulose, cellulose acetate and alginate,
   a protein polymer mixed in an amount of 1-20 parts by weight based on 100 parts by weight of the fragrance or oil, and comprising at least one material selected from the group consisting of hydrolyzed oat protein, hydrolyzed silk protein, hydrolyzed keratin, hydrolyzed elastin and hydroxypropyl trimonium hydrolyzed silk,
   an aliphatic polyesterpolyol mixed in an amount of 1-5 parts by weight based on 100 parts by weight of the fragrance or oil, and comprising aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol, and
   an aliphatic crosslinking agent mixed in an amount of 0.1-5 parts by weight based on 100 parts by weight of the fragrance or oil, and comprising at least one material selected from the group consisting of 4,4'-dicyclohexylmethane diisocyanate, trans-1,4-cyclohexanediisocyanate, hexamethylene diisocyanate, trimethylhexamethylene diisocyanate and 1,3-bis(isocyanatomethyl)-cyclohexane, constitutes the capsule wall of the capsule.

2. The biodegradable capsule of claim 1, the reaction forming the polymer further comprises an aqueous natural surfactant solution, wherein the aqueous natural surfactant solution comprises at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside, decyl glucoside, sodium cocoyl glutamate and potassium cocoyl glycinate.

3. The biodegradable capsule of claim 1, the reaction forming the polymer further comprises amino acids, wherein the amino acids comprise at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

4. A method for preparing a biodegradable capsule, the method comprising:
  (a) mixing fragrance or oil, a fibrous polymer, a protein polymer and an aliphatic polyesterpolyol;
  (b) mixing an aliphatic crosslinking agent in a mixture of the fragrance or oil, the fibrous polymer, the protein polymer and the aliphatic polyesterpolyol;
  (c) mixing and emulsifying an aqueous natural surfactant solution in the mixture of the aliphatic cross-linking agent to form an oil/water emulsion; and
  (d) adding amino acids to the oil/water emulsion and reacting to obtain a capsule,
  wherein the fibrous polymer is mixed in an amount of 1-20 parts by weight based on 100 parts by weight of the fragrance or oil, and the fibrous polymer comprises at least one material selected from the group consisting of ethyl ether cellulose, hydroxyethyl methylcellulose, hydroxybutyl methylcellulose, 2-aminoethyl 2-hydroxypropyl cellulose, hemicellulose, 6-carboxy cellulose, carboxymethyl ether cellulose, cellulose acetate and alginate,
  wherein the protein polymer is mixed in an amount of 1-20 parts by weight based on 100 parts by weight of the fragrance or oil, and the protein polymer comprises at least one material selected from the group consisting of hydrolyzed oat protein, hydrolyzed silk protein, hydrolyzed keratin, hydrolyzed elastin and hydroxypropyl trimonium hydrolyzed silk,
  wherein the aliphatic polyesterpolyol is mixed in an amount of 1-5 parts by weight based on 100 parts by weight of the fragrance or oil, and the aliphatic polyesterpolyol comprising aliphatic unsaturated polyesterpolyol which is obtained by esterification dehydration condensation reaction between at least one acid selected from the group consisting of adipic acid, azelaic acid, chlorendic acid, chlorendic anhydride, fumaric acid, isophthalic acid, phthalic anhydride, succinic acid, succinic anhydride, sebacic acid, diglycolic acid, terephthalic anhydride, citric acid, trimellitic acid, trimellitic anhydride, itaconic acid and citraconic acid, and at least one alcohol selected from the group consisting of ethylene glycol, propylene glycol, 1,3-butylene glycol, pentanediol, neopentyl glycol, hexylene glycol, diethylene glycol, dipropylene glycol, triethylene glycol, glycerol, trimethylolethane, trimethylolpropane, pentaerythritol, methylglucoside, dipentaerythritol and sorbitol,
  wherein the aliphatic crosslinking agent is mixed in an amount of 0.1-5 parts by weight based on 100 parts by weight of the fragrance or oil, and the aliphatic crosslinking agent comprises at least one material selected from the group consisting of 4,4'-dicyclohexylmethane diisocyanate, trans-1,4-cyclohexanediisocyanate, hexamethylene diisocyanate, trimethylhexamethylene diisocyanate and 1,3-bis(isocyanatomethyl)-cyclohexane.

5. The method of claim 4, wherein the aqueous natural surfactant solution is an aqueous solution obtained by mixing 1-10 parts by weight of a natural surfactant based on 100 parts by weight of fragrance or oil and adding 10-90 parts by weight of water based on 100 parts by weight of fragrance or oil, and the natural surfactant comprises at least one material selected from the group consisting of disodium laureth sulfosuccinate, cocamidopropyl betaine, lauramidopropyl betaine, sodium polyethylene glycol-7 olive oil carboxylate, sodium cocoyl apple amino acid, decyl polyglucoside, alkyl polyglucoside, babassuamidopropyl betaine, sodium lauryl sulfoacetate, sodium cocoyl isethionate, sodium cocoyl alaninate, lauryl glucoside, palm kernel/coco glucoside, decyl glucoside, sodium cocoyl glutamate and potassium cocoyl glycinate.

6. The method of claim 4, wherein the amino acids are mixed in an amount of 0.1-5 parts by weight based on 100 parts by weight of fragrance or oil, and the amino acids comprise at least one material selected from the group consisting of glycine, alanine, proline, valine, leucine, isoleucine, methionine, phenylalanine, tyrosine, tryptophan, serine, threonine, cysteine, asparagine, glutamine, lysine, histidine, arginine, aspartic acid and glutamic acid.

7. The method of claim 4, wherein pH of the oil/water emulsion is adjusted with an acid or a base in above step (c) or above step (d).

8. The method of claim 4, wherein the reaction is performed at a temperature of 30 to 50° C. in above step (d).

9. The biodegradable capsule of claim 1, the capsule has a diameter of 0.1-300 μm.

* * * * *